United States Patent
Baker et al.

(10) Patent No.: US 9,422,248 B2
(45) Date of Patent: *Aug. 23, 2016

(54) PHENYL- AND PYRIDINYL-SUBSTITUTED 2,2,2-TRIFLUOROETHANOLS HAVING ANTICONVULSANT PROPERTIES

(71) Applicant: University of Iowa Research Foundation, Iowa City, IA (US)

(72) Inventors: Max T. Baker, Iowa City, IA (US); Rajesh K. Mishra, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/407,032

(22) PCT Filed: Jun. 13, 2013

(86) PCT No.: PCT/US2013/045746
§ 371 (c)(1),
(2) Date: Dec. 10, 2014

(87) PCT Pub. No.: WO2013/188716
PCT Pub. Date: Dec. 19, 2013

(65) Prior Publication Data
US 2015/0158821 A1    Jun. 11, 2015

Related U.S. Application Data

(60) Provisional application No. 61/659,420, filed on Jun. 13, 2012.

(51) Int. Cl.
| | | |
|---|---|---|
| *A61K 31/045* | (2006.01) | |
| *C07C 31/34* | (2006.01) | |
| *C07D 239/34* | (2006.01) | |
| *C07C 39/24* | (2006.01) | |
| *C07C 43/23* | (2006.01) | |
| *C07C 43/295* | (2006.01) | |
| *C07D 213/65* | (2006.01) | |

(52) U.S. Cl.
CPC ............. *C07D 239/34* (2013.01); *C07C 39/24* (2013.01); *C07C 43/23* (2013.01); *C07C 43/295* (2013.01); *C07D 213/65* (2013.01)

(58) Field of Classification Search
CPC ............................. A61K 31/045; C07C 31/34
USPC .................. 514/345, 724, 727, 730; 546/290; 568/700, 704, 715
See application file for complete search history.

(56) References Cited

FOREIGN PATENT DOCUMENTS

WO    WO 2008/008498    1/2008

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Singh, et al. Journal of Fluorine Chemistry, 111(2), 2001, 153-160.*
PCT/US2013/045746 International Search Report and Written Opinion, issued Oct. 11, 2013.
Rajesh K. Mishra et al., "Ortho substituent effects on the anticonvulsant properties of 4-hydroxy-trifluorethyl phenols", Bioorganice & Medicinal Chemistry Letters, vol. 22, pp. 5508-5611 (Jul. 10, 2012).
Rajendra P. Singh et al., "Nucleophilic trifluoromethylation and difluorination of substituted aromatic aldehydes with Rupper's and Deoxofluor™ reagent", *Journal of Luorine Chemistry*, vol. 111, pp. 153-160 (2001).
Max T. Baker, The anticonvulsant effects of propofol and a propofol analog, 2, 6-diisopropyl-4-(1-hydroxy-2,2,2-trifluoroethyl)Phenol, in a 6Hz Partial Seizure Model, Anesthesia & Analgesia, vol. 11(2), pp. 340-344 (2011).
Yuefa Gong et al., Convenient substitution of hydroxypryridines with trifluoroacetaldehyde ethyl hemiacetal, J. Heterocyclic Chem., vol. 38(25), pp. 25-28 (2001).

* cited by examiner

*Primary Examiner* — Douglas M Willis
(74) *Attorney, Agent, or Firm* — Bryan D. Zerhusen; Locke Lord LLP

(57) ABSTRACT

A substituted phenol compound represented by Formula I:

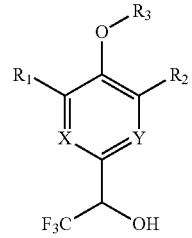

Formula I or a pharmaceutically acceptable salt or prodrug thereof. At least one of X and Y is CH, and the other one of X and Y is N or CH. $R_1$ is $C_1$-$C_4$ alkyl or $C_1$-$C_4$ haloalkyl. $R_2$ is $C_1$-$C_4$ alkyl, or halogen. $R_3$ is H, $C_1$-$C_4$ alkyl, aryl, or —$(CH_2)_n$-aryl, in which n is 1, 2, or 3. The compound is useful as anticonvulsant.

27 Claims, 1 Drawing Sheet

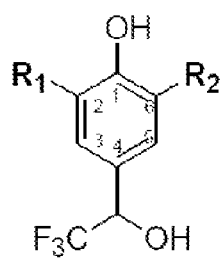
| Compound | R₁ | R₂ |
|---|---|---|
| MB003 | - CH(CH₃)₂ | - CH(CH₃)₂ |
| MB050 | - CH(CH₃)CH₂CH₃ | - CH(CH₃)CH₂CH₃ |
| DMPF | - CH₃ | - CH₃ |
| RM122 (3d) | - CH(CH₃)₂ | Br |
| RM129 (3e) | - CH(CH₃)CH₂CH₃ | Br |
| RM1204 (3c) | - CH₂CH₂CH₃ | Br |
| RM125 (4d) | - CH(CH₃)₂ | H |
| RM131 (4e) | - CH(CH₃)CH₂CH₃ | H |
| RM170 (4a) | - CH₃ | H |
| RM166 (4b) | - CH₂CH₃ | H |
| RM1208 (4c) | - CH₂CH₂CH₃ | H |

PHENYL- AND PYRIDINYL-SUBSTITUTED 2,2,2-TRIFLUOROETHANOLS HAVING ANTICONVULSANT PROPERTIES

CROSS-REFERENCE TO RELATED APPLICATIONS

This application claims the benefit of and priority to International Application No. PCT/2013/045746, filed on Jun. 13, 2013, and U.S. Provisional Patent Application No. 61/659,420, filed Jun. 13, 2012, the contents of which are incorporated herein by reference.

BACKGROUND OF THE INVENTION

Alkyl phenols have a broad range of medicinal properties ranging from central nervous system (CNS) effects to antioxidant activities. The effects of alkyl phenols on the CNS are generally sedative in nature.

2,6-Dialkylphenols having isopropyl and sec-butyl substituents are potent anesthetic/sedative compounds. For example, the dialkylphenol, propofol (2,6-diisopropylphenol) is used as an anesthetic agent in both humans and animals. This compound also serves as a muscle relaxant, anti-epileptic, anti-emetic, anti-spasmotic and as a bronchodilator. Propofol is sufficiently effective as an anticonvulsant that it is recommended for the acute treatment of status epilepticus in humans. The anticonvulsant effects of propofol and of the related compound, 2,6-di-secbutylphenol, have been confirmed in animal seizure models. 2,6-Di-sec-butylphenol (R,R) is currently undergoing development as an anesthetic due to its anesthetic potency and low cardiovascular side effects.

It was previously demonstrated that the addition of a 4-(1-hydroxy-2,2,2-trifluoroethyl) group (4-HTFE) to propofol (MB003) (FIG. 1) results in a compound that is also anticonvulsant. Anticonvulsant screening revealed that this 4-HTFE phenol is protective in the mouse 6 Hz (32 mA) model of partial epilepsy, whereas they have little to no protective effects in the mouse maximal electroshock (MES) and subcutaneous Metrazol (scMET) models. The 6 Hz model is considered an important animal model for therapy-resistant epilepsy. Therapy-resistant epilepsy is defined as cases of epilepsy that are not satisfactorily treated with available agents. This anticonvulsant profile, effectiveness in the 6 Hz model, but not in MES and scMET models, is similar to the profile of the successful anticonvulsant levetiracetam.

Propofol and 2,6-di-sec-butylphenol's potent sedative effects, properties considered toxic for anticonvulsant compounds, limit their usefulness in the more widespread treatment of seizures, and new compounds for use in therapy are needed.

SUMMARY OF THE INVENTION

In one aspect, the invention provides a compound represented by the formula (Formula I):

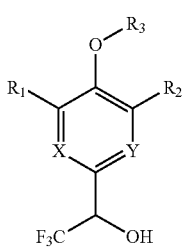

Formula I in which
X and Y are each independently N or CH;
$R_1$ is $C_1$-$C_4$ alkyl or $C_1$-$C_4$ haloalkyl;
$R_2$ is H, $C_1$-$C_4$ alkyl, or halogen; and
$R_3$ is H, $C_1$-$C_4$ alkyl, aryl, or —$(CH_2)_n$-aryl, in which n is 1, 2, or 3;
with the proviso that if X and Y are both CH, and $R_3$ is H, then $R_2$ is not $C_1$-$C_4$ alkyl;
or a pharmaceutically acceptable salt or prodrug thereof.

In certain embodiments, $R_1$ is $C_1$-$C_4$ alkyl. In certain embodiments, $R_2$ is H or halogen. In certain embodiments, $R_2$ is Br.

In one aspect, the invention provides a compound represented by the formula (Formula Ia):

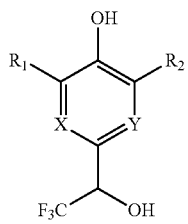

Formula Ia in which
X and Y are each independently N or CH;
$R_1$ is $C_1$-$C_4$ alkyl or $C_1$-$C_4$ haloalkyl;
$R_2$ is H, $C_1$-$C_4$ alkyl, or halogen;
with the proviso that if X and Y are both CH, then $R_2$ is not $C_1$-$C_4$ alkyl;
or a pharmaceutically acceptable salt or prodrug thereof.

In certain embodiments, $R_1$ is $C_1$-$C_4$ alkyl. In certain embodiments, $R_2$ is H or halogen. In certain embodiments, $R_2$ is Br.

In certain embodiments, the compound of Formula I is represented by Formula II:

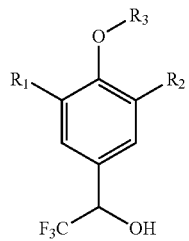

Formula II in which $R_1$, $R_2$ and $R_3$ are as defined for Formula I.

In certain embodiments, the compound of Formula I or Ia is represented by Formula IIa:

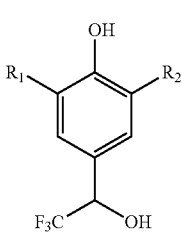

Formula IIa in which $R_1$ and $R_2$ are as defined for Formula I.

In certain embodiments, the compound of Formula I is represented by Formula III:

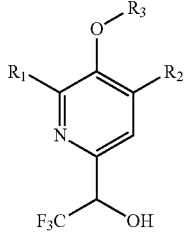

Formula III in which $R_1$, $R_2$ and $R_3$ are as defined for Formula I.

In certain embodiments, the compound of Formula I or Ia is represented by Formula IIIa:

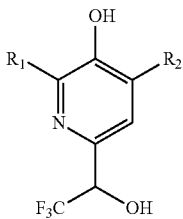

Formula IIIa in which $R_1$ and $R_2$ are as defined for Formula I.

In certain embodiments, the compound of Formula I is represented by Formula IV:

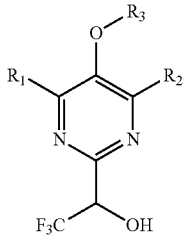

Formula IV in which $R_1$, $R_2$ and $R_3$ are as defined for Formula I.

In certain embodiments, the compound of Formula I or Ia is represented by Formula IVa:

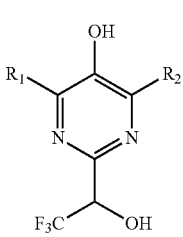

Formula IVa in which $R_1$ and $R_2$ are as defined for Formula I.

In certain embodiments, the invention provides a compound represented by the formula (Formula V):

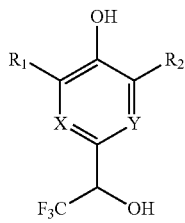

Formula V in which

X and Y are each independently N or CH;

$R_1$ is $C_1$-$C_4$ alkyl or $C_1$-$C_4$ haloalkyl;

$R_2$ is H or halogen;

or a pharmaceutically acceptable salt or prodrug thereof.

In another aspect, the invention provides a pharmaceutical composition including a compound of any one of Formula I-V and a pharmaceutically acceptable carrier.

In another aspect, the invention provides a use of compound of any of Formulae I-V for the preparation of a medicament.

In another aspect, the invention provides a method treating or preventing convulsions in a subject in need thereof. The method includes administering a pharmaceutically effective amount of a compound of Formula I-V or FIG. 1 to the subject.

In another aspect, the invention provides a method of treating or preventing seizures in a subject in need thereof, the method comprising administering a therapeutically effective amount of a pharmaceutical composition of a compound of Formula I-V to the subject.

In another aspect, the invention provides a method of treating or preventing epileptic seizures in a subject in need thereof, the method comprising administering a therapeutically effective amount of a pharmaceutical composition of a compound of Formula I-V to the subject.

In another aspect, the invention provides a method for preventing cellular damage from oxygen radicals, the method comprising contacting a cell in need of such treatment with an effective amount of a compound of the invention under conditions such that cellular damage from oxygen free radicals is prevented.

In another aspect, the invention provides a method of treating a respiratory disorder in a subject in need thereof, the method comprising administering to the subject an effective amount of a compound of the invention.

In another aspect, the invention provides a method of treating or preventing pain in a subject in need thereof, the method comprising administering to the subject an effective amount of a compound of the invention.

Other aspects and embodiments of the invention will be apparent from the description, drawings, and claims herein.

BRIEF DESCRIPTION OF THE DRAWINGS

FIG. 1 is a table showing the structures of certain compounds according to the present invention.

DETAILED DESCRIPTION OF THE INVENTION

I. Compounds

In one aspect, the invention provides substituted trifluoromethylhydroxymethylphenols.

In one aspect, the invention provides a compound represented by the formula (Formula I):

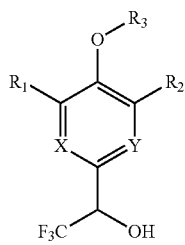

Formula I in which

X and Y are each independently N or CH;

$R_1$ is $C_1$-$C_4$ alkyl or $C_1$-$C_4$ haloalkyl;

$R_2$ is H, $C_1$-$C_4$ alkyl, or halogen; and $R_3$ is H, $C_1$-$C_4$ alkyl, aryl, or —$(CH_2)_n$-aryl, in which n is 1, 2, or 3;

with the proviso that if X and Y are both CH, and $R_3$ is H, then $R_2$ is not $C_1$-$C_4$ alkyl;

or a pharmaceutically acceptable salt or prodrug thereof.

In certain embodiments, $R_1$ is $C_1$-$C_4$ alkyl. In certain embodiments, $R_2$ is H or halogen. In certain embodiments, $R_2$ is Br.

In one aspect, the invention provides a compound represented by the formula (Formula Ia):

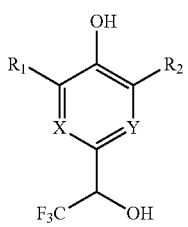

Formula Ia in which

X and Y are each independently N or CH;

$R_1$ is $C_1$-$C_4$ alkyl or $C_1$-$C_4$ haloalkyl;

$R_2$ is H, $C_1$-$C_4$ alkyl, or halogen;

with the proviso that if X and Y are both CH, then $R_2$ is not $C_1$-$C_4$ alkyl;

or a pharmaceutically acceptable salt or prodrug thereof.

In certain embodiments, $R_1$ is $C_1$-$C_4$ alkyl. In certain embodiments, $R_2$ is H or halogen. In certain embodiments, $R_2$ is Br.

In certain embodiments, the compound of Formula I is represented by Formula II:

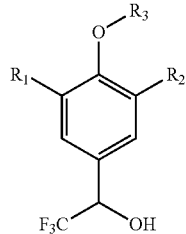

Formula II in which $R_1$, $R_2$ and $R_3$ are as defined for Formula I.

In certain embodiments, the compound of Formula I, Ia, or II is represented by Formula IIa:

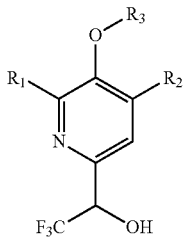

Formula IIa in which $R_1$ and $R_2$ are as defined for Formula I.

In certain embodiments, the compound of Formula I is represented by Formula III:

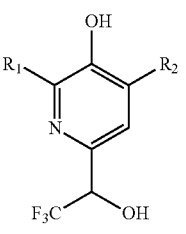

Formula III in which $R_1$, $R_2$ and $R_3$ are as defined for Formula I.

In certain embodiments, the compound of Formula I, Ia, or III is represented by Formula IIIa:

Formula IIIa in which $R_1$ and $R_2$ are as defined for Formula I.

In certain embodiments, the compound of Formula I is represented by Formula IV:

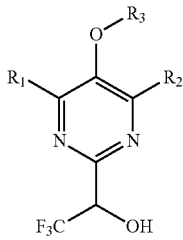

Formula IV in which $R_1$, $R_2$ and $R_3$ are as defined for Formula I.

In certain embodiments, the compound of Formula I, Ia or IV is represented by Formula IVa:

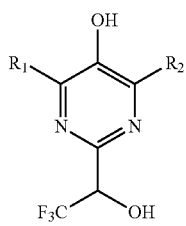

Formula IVa in which $R_1$ and $R_2$ are as defined for Formula I.

In certain embodiments, the invention provides a compound represented by the formula (Formula V):

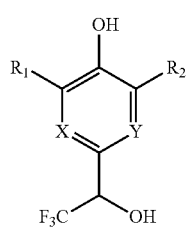

Formula V in which
X and Y are each independently N or CH;
$R_1$ is $C_1$-$C_4$ alkyl or $C_1$-$C_4$ haloalkyl;
$R_2$ is H or halogen;
or a pharmaceutically acceptable salt or prodrug thereof.

In certain embodiments of the compounds of any of Formulae I-V, $R_1$ is $C_1$-$C_4$ alkyl.

In certain embodiments of the compounds of any of Formulae I-V, $R_2$ is H or halogen.

In certain embodiments of the compounds of any of Formulae I-V, $R_2$ is Br.

In certain embodiments of the compounds of any of Formulae I-V, $R_1$ is $C_1$-$C_4$ alkyl and $R_2$ is H or halogen. In certain embodiments of the compounds of any of Formulae I-V, $R_1$ is $C_1$-$C_4$ alkyl and $R_2$ is Br. In certain embodiments of the compounds of any of Formulae I-V, $R_1$ is $C_3$-$C_4$ alkyl.

In certain embodiments, the compound is selected from the group consisting of 2-Bromo-6-isopropyl-4-(2,2,2-trifluoro-1-hydroxy-ethyl)-phenol (RM122), 2-Bromo-6-sec-Butyl-4-(2,2,2-trifluoro-1-hydroxy-ethyl)-phenol (RM129), 2-Bromo-6-n-propyl-4-(2,2,2-trifluoro-1-hydroxy-ethyl)-phenol (RM1204), 2-iso-Propyl-4-(2,2,2-trifluoro-1-hydroxy-ethyl)-phenol (RM125), 2-sec-Butyl-4-(2,2,2-trifluoro-1-hydroxy-ethyl)-phenol (RM-131), 2-Methyl-4-(2,2,2-trifluoro-1-hydroxy-ethyl)-phenol (RM170), 2-Ethyl-4-(2,2,2-trifluoro-1-hydroxy-ethyl)-phenol (RM-166), or 2-n-Propyl-4-(2,2,2-trifluoro-1-hydroxy-ethyl)-phenol (RM-1208).

In certain embodiments, the compound is selected from the group consisting of:

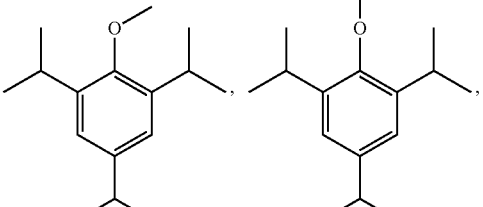
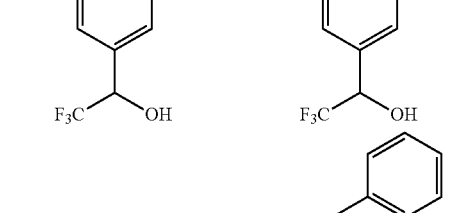
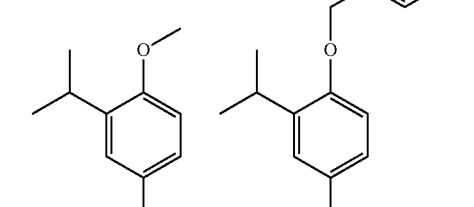
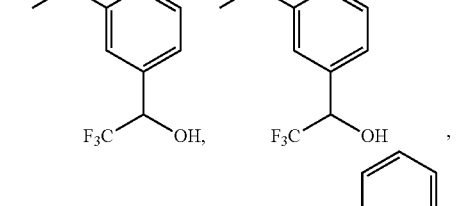
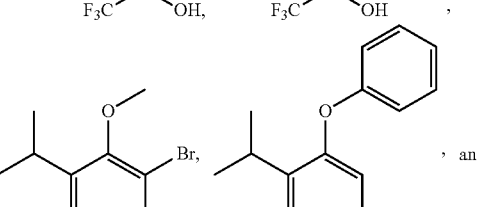
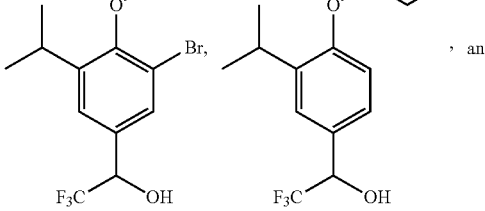
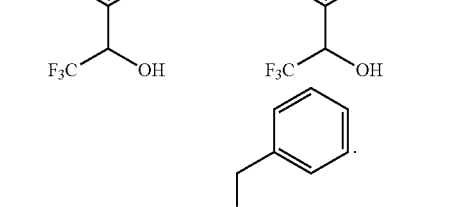
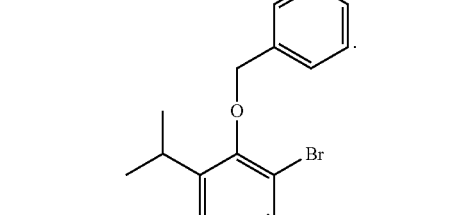

It will be appreciated that the compounds of the present invention (e.g., compounds of Formula I-V), may contain one or more asymmetric carbon atoms. As such, compounds of this invention can exist as either individual enantiomers or diastereomers, or as mixtures of two enantiomers or two or more diastereomers. Accordingly, a compound of the present invention will include both racemic mixtures, and also individual respective enantiomers or stereoisomers that are substantially free from one or more other possible enantiomers or stereoisomers. The term "substantially free of other enantiomers or stereoisomers" as used herein means less than 25% of other enantiomers or stereoisomers, preferably less than 10% of other enantiomers or stereoisomers, more preferably less than 5% of other enantiomers or stereoisomers and most preferably less than 2% of other enantiomers or stereoisomers, or less than "X"% of other enantiomers or stereoisomers (wherein X is a number between 0 and 100, inclusive), are present. Methods of obtaining or synthesizing an individual enantiomer or diastereomer for a given compound are well known in the art and may be applied as practicable to final compounds or to starting material or intermediates. For example, chiral chromatography or crystallization of a salt formed with an optical active acid or base can be used to separate many enantiomers.

In another aspect, the invention provides a pharmaceutical composition including a compound of Formula I-V together with a pharmaceutically acceptable carrier.

It has been found that certain 4-HTFE-substituted phenols have reduced sedative effects, such that anticonvulsant effects occur at doses where animals can maintain a gait on the rotorod. This is reflected in wider protective indices (TD50/ED50).

In another aspect, the invention provides a method of treating or preventing seizures, such as epileptic seizures, or convulsions in a subject in need thereof. The method includes administering a pharmaceutically effective amount of a compound of Formula I-V or FIG. 1 to the subject.

In another aspect, the invention provides a method for preventing cellular damage from oxygen radicals. The method includes the step of contacting a cell in need of such treatment with an effective amount of a compound of Formula I-V under conditions such that cellular damage from oxygen free radicals is prevented.

It has been found that certain compounds (such as compound 10),

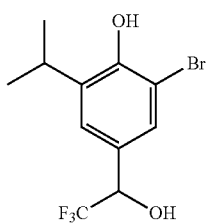

have analgesic properties. Thus, in another aspect, the invention provides a method of providing analgesia or treating or preventing pain in a subject in need thereof, the method comprising administering to the subject an effective amount of a compound of Formula I-V.

In another aspect, the invention provides a method of preparing a compound of Formula (IIa). The method includes the step of reacting a phenolic compound of the formula (Formula VI):

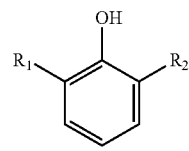

in which $R_1$ and $R_2$ are as described above, with a $C_2$-hydroxyhaloalkylating agent under conditions such that the compound of Formula IIa is prepared.

In certain embodiments, the $C_2$-haloalkylating agent is trifluoroacetaldehyde ethyl hemiacetal. In certain embodiments, wherein the reacting step includes reacting the compound of Formula IIa with the $C_2$-haloalkylating agent in the presence of a base or Lewis acid catalyst. In certain embodiments, the base catalyst is potassium carbonate. In certain embodiments, the Lewis acid catalyst in $ZnCl_2$ or $ZnI_2$. In certain embodiments, compounds of Formulas I-V where $R_3$ is $C_1$-$C_4$ alkyl, aryl, or —$(CH_2)_n$-aryl (in which n is 1, 2, or 3) are obtained by starting with appropriate para-hydroxy benzaldehydes.

Definitions

The term "alkyl," as used herein, refers to the radical of saturated aliphatic groups, including straight-chain alkyl groups, branched-chain alkyl groups, and cycloalkyl (alicyclic) groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), preferably 20 or fewer, and more preferably 10 or fewer, and still more preferably 6 or fewer. Similarly, preferred cycloalkyls have from 3-10 carbon atoms in their ring structure, and more preferably have 3, 4, 5, 6 or 7 carbons in the ring structure.

Moreover, the term "alkyl" as used throughout the specification and claims is intended to include both "unsubstituted alkyls" and "substituted alkyls," unless otherwise specified. The term "substituted alkyls" refers to alkyl moieties having substituents replacing a hydrogen on one or more carbons of the hydrocarbon backbone (e.g., one to 2n+1 substituents, where n is the number of carbons in the hydrocarbon backbone, and more preferably one to three substituents). Such substituents can include, for example, halogen (i.e., F, Cl, Br, or I), hydroxyl, alkoxy, cyano, amino, sulfhydryl, alkylthio, nitro, or azido moieties. It will be understood by those skilled in the art that the moieties substituted on the hydrocarbon chain can themselves be substituted, if appropriate. Cycloalkyls can be further substituted, e.g., with the substituents described above. The term "alkyl" also includes unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six, and most preferably from one to four carbon atoms in its backbone structure (if straight chain), or from three to six carbon atoms in its backbone structure (if branched chain). Examples of lower alkyl groups include methyl, ethyl, n-propyl, i-propyl, tert-butyl, hexyl, heptyl, octyl and so forth. In a preferred embodiment, the term "lower alkyl" includes a straight chain alkyl having 4 or fewer carbon atoms in its backbone, e.g., $C_1$-$C_4$ alkyl.

The term "haloalkyl," as used herein, refers to an alkyl group having one or more (preferably 1 to 3) halogen atoms attached to the alkyl carbon chain. In certain embodiments, a haloalkyl group has 1 to 3 fluorine atoms or chlorine atoms attached to the alkyl carbon chain. In a preferred embodiment, a haloalkyl contains at least one fluorine; an alkyl or haloalkyl group containing at least one fluorine atom is referred to herein as a "fluoroalkyl" group. Preferred fluoroalkyl groups include monofluoromethyl, difluoromethyl, trifluoromethyl and perfluoroethyl.

The term "hydroxyhaloalkylating agent," as used herein, refers to a reagent which can be reacted with a phenolic compound to functionalize the phenol compound with a hydroxyhaloalkyl group through a carbon-carbon bond. A "$C_2$-hydroxyhaloalkylating agent" is a hydroxyhaloalkylating agent which reacts with a phenolic compound and results in the addition of a $C_2$-(1-hydroxyl)haloalkyl moiety to the phenolic compound. In general, a hydroxyhaloalkylating agent will include a reactive moiety and a haloalkyl chain. The reactive moiety can be, e.g., a hemiacetal, alkyl halides, tosylates, and the like.

The term "aryl", as used herein, refers to a monocyclic or bicyclic ring system having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

Aryl groups may be carbocyclic or heterocyclic. The term "heteroaryl" refers to an aryl ring having 5 to 10 ring atoms, preferably 5, 6, or 9 ring atoms; having 6, 10, or 14 π electrons shared in a cyclic array; and having, in addition to carbon atoms, from one to five heteroatoms in a ring. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The term "heteroaryl", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono- or bicyclic. The term "heteroaryl" may be used interchangeably with the terms "heteroaryl ring," "heteroaryl group," or "hetero aromatic".

An aryl group (including carbocyclic aryl groups and heteroaryl groups) may optionally be substituted on an aromatic ring with one to three substituents selected from halogen, $C_1$-$C_4$ alkyl, $C_1$-$C_4$ haloalkyl, $C_1$-$C_4$ alkoxy, —CN, $NO_2$, and the like.

The term "prodrug, as used herein, refers to a compound which is administered to a subject and can be metabolized to provide a compound of the invention in vivo. For example, a phenolic ester can be cleaved in vivo to release a phenolic compound of the invention.

The term "sedation," as used herein, refers to the calming of mental excitement or abatement of physiological function by administration of a drug. The term "sedating" refers to the induction of sedation.

The term "subject" or "patient," as used herein, refers to an animal, preferably a mammal, more preferably a dog, cat, monkey, horse, cow, sheep, or pig, and, in certain preferred embodiments, a human.

Examples of preferred compounds of the invention include the following:

| Compound | $R_1$ | $R_2$ |
|---|---|---|
| MB003 | —CH(CH$_3$)$_2$ | —CH(CH$_3$)$_2$ |
| MB050 | —CH(CH$_3$)CH$_2$CH$_3$ | —CH(CH$_3$)CH$_2$CH$_3$ |
| DMPF | —CH$_3$ | —CH$_3$ |
| RM122 (3d) | —CH(CH$_3$)$_2$ | Br |
| RM129 (3e) | —CH(CH$_3$)CH$_2$CH$_3$ | Br |
| RM1204 (3c) | —CH$_2$CH$_2$CH$_3$ | Br |
| RM125 (4d) | —CH(CH$_3$)$_2$ | H |
| RM131 (4e) | —CH(CH$_3$)CH$_2$CH$_3$ | H |
| RM170 (4a) | —CH$_3$ | H |
| RM166 (4b) | —CH$_2$CH$_3$ | H |
| RM1208 (4c) | —CH$_2$CH$_2$CH$_3$ | H |

In certain embodiments, the compound is selected from the group consisting of:

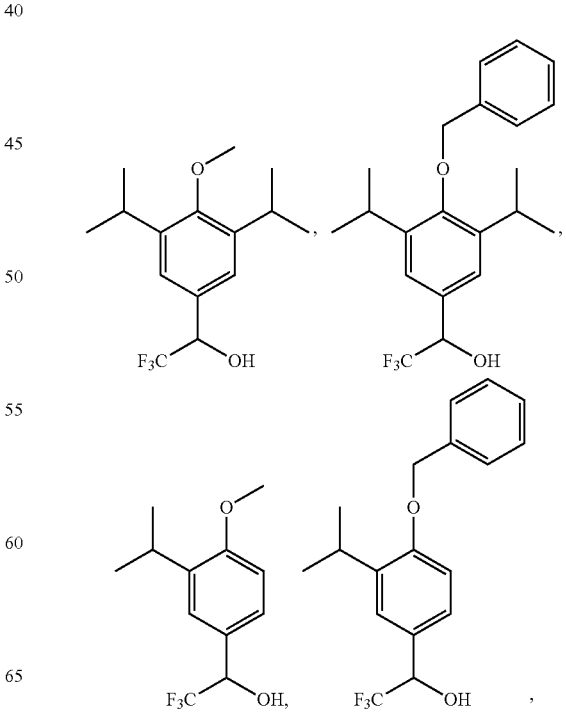

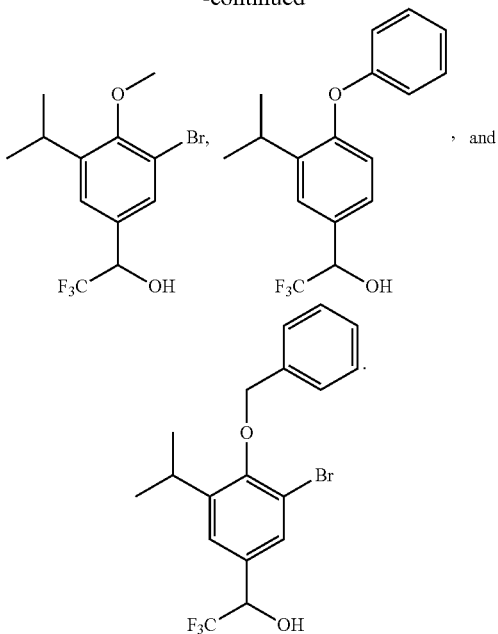

These compounds are:
1-(3,5-diisopropyl-4-methoxyphenyl)-2,2,2-trifluoroethanol,
1-(4-(benzyloxy)-3,5-diisopropylphenyl)-2,2,2-trifluoroethanol,
2,2,2-trifluoro-1-(3-isopropyl-4-methoxyphenyl)ethanol,
1-(4-(benzyloxy)-3-isopropylphenyl)-2,2,2-trifluoroethanol,
1-(3-bromo-5-isopropyl-4-methoxyphenyl)-2,2,2-trifluoroethanol,
2,2,2-trifluoro-1-(3-isopropyl-4-phenoxyphenyl)ethanol, and
1-(4-(benzyloxy)-3-bromo-5-isopropylphenyl)-2,2,2-trifluoroethanol.

II. Synthesis

The compounds of the invention can be made by a variety of methods, some of which are known in the art. For example, certain compounds of the invention can be made as described in the Examples herein, in which a 2-substituted phenol is treated with a hemiacetal of a halogenated (e.g., chloroalkyl or fluoroalkyl) aldehyde, preferably in the presence of a catalytic amount of a base, such as potassium carbonate, or a Lewis acid such as boron trifluoride ($BF_3$), aluminum trichloride, zinc chloride ($ZnCl_2$), or zinc iodide ($ZnI_2$). See, e.g., Gong et al., *Bull. Chem. Soc. Japan.* 74, 377-383 (2001). This reaction is illustrated in Scheme 1 using trifluoroacetaldehyde ethyl hemiacetal to produce para substitution of a 2,6-disubstituted phenol 2, resulting in product 3. Other haloaldehyde hemiacetals, such as difluoroacetaldehyde ethyl hemiacetal (or other reactive alkylating agents) may be employed. Para-substitution of the phenol ring was generally found to be high using potassium carbonate as catalyst.

As also shown in FIG. 1, the resulting 4-hydroxyalkylphenol 3 can be reduced, e.g., using standard conditions such as hydrogen in the presence of a palladium catalyst, and the like, to produce the 2-substituted phenol 4. Compound 4 can be further reacted, if desired, to produce a variety of compounds of the invention.

In certain embodiments, compounds of Formulas I-V where $R_3$ is $C_1$-$C_4$ alkyl, aryl, or alkylaryl (including benzyl) are obtained. These compounds can be prepared starting with the appropriate para-hydroxy benzaldehydes. For example, alkyl and —$(CH_2)_n$-aryl ethers can be derivatized by coupling para-hydroxy benzaldehydes with alkyl halides and arylalkyl halides, respectively, using a suitable base to form the ether. Alkylaryl ethers (including benzyl ethers) can also be obtained by Mitsunobu coupling of appropriate para-hydroxy benzaldehydes with an alcohol of the formula HO—$(CH_2)_n$-aryl, in which n is 1, 2, or 3. Aryl ethers can be prepared by copper-catalyzed coupling of para-hydroxy benzaldehydes with aryl boronic acids. The para-ether benzaldehydes on treatment with trifluorotrimethylsilane and tetrabutylammonium fluoride yield the desired trifluoromethyl hydroxy ether compounds.

Example 2 provides exemplary synthetic methods for preparing the compounds of the invention.

The structures of compounds can be confirmed using standard analytical techniques such as mass spectrometry and NMR.

Some of the novel compounds of this invention can be prepared using synthetic chemistry techniques well known in the art (see, e.g., *Comprehensive Organic Synthesis*, Trost, B. M. and Fleming, I. eds., Pergamon Press, Oxford).

III. Pharmaceutical Compositions

The invention also provides pharmaceutical compositions. The pharmaceutical compositions include an effective amount of a compound of the invention (e.g., a compound of Formula I-V or FIG. 1) and a pharmaceutically acceptable carrier. In certain embodiments, a pharmaceutical composition of the invention further includes one or more additional anesthetic or sedative agent.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those compounds of the invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In certain embodiments, the pharmaceutically acceptable carrier can be a formulation vehicles similar to those used for propofol, e.g., emulsions, polymeric micelles, cyclodextrins, and the like.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound(s) of the invention include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 0.5% percent to about 5% percent for parenteral administration.

Methods of preparing these compositions include the step of bringing into association a compound(s) of the invention with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound(s) of the invention as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compound(s) of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active compound(s) of the invention may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compound(s) of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound(s) of the invention include powders, sprays, ointments, pastes, creams, lotions, gels, solutions, patches and inhalants. The active compound(s) of the invention may be mixed under sterile conditions with a pharmaceutically-acceptable carrier, and with any preservatives, buffers, or propellants which may be required.

The ointments, pastes, creams and gels may contain, in addition to compound(s) of the invention of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound(s) of the invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound(s) of the invention can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a compound(s) of the invention to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions of the invention suitable for parenteral administration comprise one or more compound(s) of the invention in combination with one or more pharmaceutically-acceptable sterile isotonic aqueous or nonaqueous solutions, dispersions, suspensions or emulsions (including oil-in-water emulsions), polymeric micelles, cyclodextrin complexes, liposomes, protein nanoparticle formulations, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of compound(s) of the invention in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compound(s) of the invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compound(s) of the invention, which may be used in a suitable hydrated form, and/or the pharmaceutical compositions of the present invention, are formulated into pharmaceutically-acceptable dosage forms by conventional methods known to those of skill in the art.

IV. Methods of Use

The compounds of the invention can be used in a variety of methods. The compounds of the invention can be used, e.g., as antioxidants, muscle relaxants (e.g., as bronchodilators), antispasmotics, inhibitors of endocannabinoid catabolism, and anti-nauseants. For discussion of certain methods in which the novel compounds and compositions of the invention may be useful, see, e.g., U.S. Patent Publication No. 2003-0176513, incorporated herein by reference herein.

In one aspect, the invention provides a method treating or preventing convulsions in a subject in need thereof. The method includes administering a pharmaceutically effective amount of a compound of Formula I-V or FIG. 1 to the subject.

In another aspect, the invention provides a method of treating or preventing seizures in a subject in need thereof, the method comprising administering a therapeutically effective amount of a pharmaceutical composition of a compound of Formula I-V to the subject.

In another aspect, the invention provides a method of treating or preventing epileptic seizures in a subject in need thereof, the method comprising administering a therapeutically effective amount of a pharmaceutical composition of a compound of Formula I-V to the subject.

In another aspect, the invention provides a method of treating or preventing pain in a subject in need thereof, the method comprising administering to the subject an effective amount of a compound of Formula I-V.

In still another aspect, the invention provides a method for reducing the level of oxygen free radicals in a tissue. The method includes the step of contacting a tissue (whether in vivo or in vitro) with an effective amount of a compound of the invention under conditions such that the level of oxygen free radicals in the tissue is reduced.

In still another aspect, the invention provides a method for preventing cellular damage from oxygen radicals. The method includes the step of contacting a cell in need of such treatment (whether in vivo or in vitro) with an effective amount of a compound of the invention under conditions such that cellular damage from oxygen free radicals is prevented.

The compounds of the invention can be used as anti-oxidants. Oxidants are introduced into an organism through the environment (e.g., upon exposure to sunlight), by smoke inhalation and also are generated during an inflammatory response. When cells are subjected to oxidative stress, cellular functions can be globally affected.

Free radicals produced during oxidative stress can react with proteins, nucleic acids, lipids, and other biological macromolecules producing damage to cells and tissues. Free radicals are atoms, ions, or molecules that contain an unpaired electron (Pryor, 1976, Free Radicals in Biol. 1: 1). Free radicals are usually unstable and exhibit short half-lives. Elemental oxygen is highly electronegative and readily accepts single electron transfers from cytochromes and other reduced cellular components. For example, a portion of the $O_2$ consumed by cells engaged in aerobic respiration is univalently reduced to superoxide radical ($O_2^-$) (Cadenas, 1989, Ann. Rev. Biochem. 58: 79). Sequential univalent reduction of $O_2^-$ produces hydrogen peroxide ($H_2O_2$), hydroxyl radical, and water.

Free radicals can originate from many sources, including aerobic respiration, cytochrome P-450-catalyzed monooxygenation reactions of drugs and xenobiotics (e.g., trichloromethyl radicals, $CCl_3$, formed from oxidation of carbon tetrachloride), and ionizing radiation. For example, when tissues are exposed to gamma radiation, most of the energy deposited in the cells is absorbed by water and results in scission of the oxygen-hydrogen covalent bonds in water, leaving a single electron on hydrogen and one on oxygen creating two radicals: H and OH.

The hydroxyl radical is the most reactive radical known in chemistry. It reacts with biomolecules and sets off chain reactions and can interact with the purine or pyrimidine bases of nucleic acids. Radiation-induced carcinogenesis may be initiated by free radical damage (Breimer, 1988, Brit. J. Cancer 57: 6). The "oxidative burst" of activated neutrophils produces abundant superoxide radicals, which re believed to be an essential factor in producing the cytotoxic effect of activated neutrophils. Reperfusion of ischemic tissues also produces large concentrations of free oxygen radical, typically superoxide (Gutteridge et al., 1990, Arch. Biochem. Biophys. 283: 223). Moreover, superoxide may be produced physiologically by endothelial cells for reaction with nitric oxide, a physiological regulator, forming peroxynitrite, which may decay and give rise to hydroxyl radical (Marletta, 1989, Trends Biochem. Sci. 14: 488; Moncada et al., 1989, Biochem. Pharmacol. 38: 1709; Saran et al., 1990, Free Rad. Res. Commun. 10: 221; Beckman et al., 1990, Proc. Natl. Acad. Sci. USA 87: 1620). Additional sources of free oxygen radicals derive from "leakage" of electrons from disrupted mitochondrial or endoplasmic reticular electron transport chains, prostaglandin synthesis, oxidation of catecholamines, and platelet activation.

Oxygen, though essential for aerobic metabolism, can be converted to poisonous metabolites, such as the superoxide anion and hydrogen peroxide, collectively known as reactive oxygen species (ROS). Increased ROS formation under pathological conditions is believed to cause cellular damage through the action of these highly reactive molecules on proteins, lipids, and DNA. During inflammation, ROS are generated by activated phagocytic leukocytes; for example, during the neutrophil "respiratory burst", superoxide anion is generated by the membrane-bound NADPH oxidase. ROS are also believed to accumulate when tissues are subjected to ischemia followed by reperfusion.

Many free radical reactions are highly damaging to cellular components; they crosslink proteins, mutagenize DNA, and peroxidize lipids. Once formed, free radicals can interact to produce other free radicals and non-radical oxidants such as singlet oxygen and peroxides. Degradation of some of the products of free radical reactions can also generate potentially damaging chemical species. For example, malondialdehyde is a reaction product of peroxidized lipids that reacts with virtually any amine-containing molecule. Oxygen free radicals also cause oxidative modification of proteins (Stadtman, 1992, Science 257: 1220).

A pharmaceutically effective amount of the compounds described herein can be used prophylactically or in treatment regimens for inhibition of oxidation in subjects that are at risk for developing a disease related to oxidative stress, such as cancer. Further, many neurodegenerative diseases such as Alzheimer's disease, Huntington's disease, Pick disease, multiple sclerosis, and others are associated with oxidative stress. Additional free radical-associated diseases include, but are not limited to: ischemic reperfusion injury, inflammatory diseases (discussed further below), systemic lupus erythematosis, myocardial infarction, stroke, traumatic hemorrhage, spinal cord trauma, cataract formation, uveitis, emphysema, gastric ulcers, oxygen toxicity, neoplasia, undesired cell apoptosis, and radiation sickness (see, e.g., U.S. Pat. No. 5,827,880).

A pharmaceutically effective amount for anti-oxidant activity may range from about 100 mg to 1 g of the compound.

Initial doses of the compounds of the invention can be determined by a variety of in vitro and in vivo assays. For example, compounds can be tested for their ability to quench free oxygen radicals generated by photo-illumination of riboflavin (see, e.g., Kubow, 1992, Free Radical Biology and Medicine 12: 63-81; Frankel, 1984; JAOCS 61: 1908-1917; U.S. Pat. No. 6,132,711) or by determining the formation of malondialdehyde degradation products of arachidonic acid after exposure of arachidonic acid to light (see, e.g., U.S. Pat. No. 5,912,179). Electron spin resonance spectroscopy also can be used to verify the formation of phenoxyl radicals of fluorine-substituted alkyl phenols in the presence of free radicals.

Cell-based assays also can be used. In one aspect, a compound of the invention of the invention has antioxidant activity if the compound, when added to a cell culture or assay reaction (a "test reaction") produces a detectable decrease in the amount of a free radical, such as superoxide, or a non-radical reactive oxygen species, such as hydrogen peroxide, as compared to a parallel cell culture or assay reaction that is not treated with the compound ("control reactions"). As used herein, a "detectable decrease" is one which is significantly different from the amount of free radical concentrations observed in control reactions using routine statistical tests known in the art and setting p values to <0.05. In one aspect, a detectable decrease is an at least 10% decrease in the amount of a free radical in a test reaction compared to a control reaction, and preferably, a 20%, 30%, 40%, or 50% or greater, reduction.

Suitable concentrations (i.e., an effective dose) in vivo can be determined by various methods, including generating an empirical dose-response curve, predicting potency and efficacy and through other methods used in the pharmaceutical sciences. Since oxidative damage is generally cumulative, there is no minimum threshold level (or dose) with respect to efficacy, although minimum doses for producing a detectable therapeutic or prophylactic effect for particular disease states can be established, as described further below.

As discussed above, the inflammatory response that occurs in mammals involves an oxidative component. Thus, the compounds of the invention of this invention are useful as anti-inflammatory agents.

In general, the inflammatory response of mammals is dependent on a variety of inflammatory mediators. Many of these mediators, for example, cytokines, TNF-alpha and IL-2, and the eicosanoids, prostacyclins, thromboxanes and leukiotrienes require an oxidation reaction for their production. A pharmacologically effective amount of a compound of the invention would inhibit production of these inflammatory mediators and can be administered to subjects where an anti-inflammatory effect is desired. Some examples of inflammatory disorders which can be treated using compounds according to the invention, include, but are not limited to: arthritis, inflammation caused by respiratory diseases or environmental factors, inflammation due to trauma (including complications from surgery), and inflammation caused by disorders of the central nervous system.

Examples of respiratory disorders that can be treated with the fluorinated alkyl phenol compounds include, cystic fibrosis, emphysema, HIV-associated lung disease, chronic obstructive pulmonary disease, asthma, bronchiolitis, bronchopulmonary dysplasia, lung cancer, respiratory distress syndrome (ARD), acid aspiration, idiopathic pulmonary fibrosis, immune-complex-mediated lung injury, ischemia-reperfusion injury, mineral dust pneumoconiosis, Silo-Fillers disease, and others. The preferred method for treatment of these disorders is through the administration of compounds of the invention to the respiratory tract by using an inhalation device.

A pharmaceutically effective amount of compound delivered as an inhalant ranges from about 0.1 mg to 10 mg per inhalation, several times daily. An oral dose can range from about 1 mg to 500 mg.

In vitro and/or in vivo assays may be used to optimize compounds according to the invention. For example, a bead embolization model of pulmonary inflammation can be used in which antigens are coupled to Sepharose beads, which are embolized to the lungs of mice via injection into their tail veins. The animals preferably are pre-sensitized to the coupled antigen. The immune system of the mouse then mounts a vigorous immune response to the antigen-coupled bead. Focal inflammatory responses, which can last for several weeks, can be examined by examining lung tissue for the size of an embolus and for cytokine production. Hilar lymph nodes and spleens also can be examined. In one aspect, the efficacy of a compound of the invention is determined by monitoring decreases in focal inflammatory responses. Preferably, a therapeutically effective compound is one which decreases a focal inflammatory response as measured by the size of an embolus by at least 30% and which decreases the production of inflammatory cytokines by at least 10%, preferably, at least 20%, at least 30%, at least 40%, and at least 50%.

Other inflammatory disorders which can be treated include, but are not limited to, an autoimmune disease, inflammatory bowel disease, Crohn's disease, ulcerative colitis, a disease caused by an infection of a gram negative bacteria, a degenerative joint disease, such as osteoarthritis, rheumatoid arthritis, rheumatoid spondylitis, or gouty arthritis, asthma (including status asthmaticus), endotoxemia, sepsis, or septic shock.

The compounds of this invention also are useful in treatment of inflammation in the CNS. Inflammation in the CNS can be caused by oxidative stress, viral disease (i.e. meningitis, HIV-1 infection, HIV-II infection), and by traumatic events. Some traumas that can be treated with the compounds described herein include, but are not limited to, concussions, brain hemorrhage, edema, stroke, spinal cord injury, and hematomas.

The antioxidant properties of the compounds of the invention also can be exploited in regimens for treatment of cancer. Administration of anti-oxidants during chemotherapy has been found to aid in the inhibition of tumor growth (Chinery et al., 1997, Nature Medicine 3: 1233-1241). In addition, many chemotherapeutic agents have a side effect of promoting free radical formation and thus the general anti-oxidant activities of alkyl phenols are beneficial. In a preferred embodiment, compounds of this invention are particularly useful for treatment of cancers of the respiratory tract. Pharmaceutically effective amounts of compound used in a chemotherapy regime may range from, e.g., about 1 mg to about 500 g of compound delivered daily.

The compounds of the invention also are useful as antiemetics, which are anti-nauseants. A pharmaceutically effective dose to inhibit nausea and vomiting ranges from about 1 mg to about 500 mg.

The compounds of the invention are also useful in the treatment of seizures such as, epileptic seizures. Pharmaceutically effective anti-convulsive dosages range from about 1 mg to about 500 g daily.

In one aspect, compounds of the invention are assayed for their ability to scavenge oxygen radicals and cause other beneficial effects on cultured cells, which model inflammatory responses. The anti-inflammatory activity of compounds also may be evaluated in vivo, for example, in animal models (see, e.g., as described in Young et al., 1984, J. Invest. Dermatol., 82: 367-371; U.S. Pat. No. 6,180,796; U.S. Pat. No. 6,177,610; U.S. Pat. No. 6,114,382; and U.S. Pat. No. 6,174,901). Animal models for inflammatory bowel disease include the TNBS colitis model described in Neurath et al., 1995, J. of Exp. Med. 182: 1281; IL-2 mutant mice (e.g., Ludviksson et al., 1997, J. of Immunol. 158: 104); IL-10 mutant mice (Berg et al., 1996, J. of Clin. Investigation 98: 1010); TCR transgenic mice (Mombaerts et al., 1993, Cell 75: 274); and SCID mice comprising CD45+ T cells (Powrie et al., 1994, Immunity 1: 553). Rheumatoid arthritis models include the murine pristane-induced arthritis model (Stasluk et al., 1997, Immunol. 90: 81) and the murine collagen-induced arthritis model (Horsfall et al., 1997, J. of Immunol. 159: 5687). Insulin-dependent diabetes (type 1), an autoimmune disease, can be mimicked by NOD mice (Cameron et al., 1997, J. of Immunol. 159: 4686). Lupus can be mimicked by an (NZWXNZB) F.sub.1 mouse model (Santiago et al., 1997, J. of Exp. Med. 185: 65) and by a GRD, LPR mouse (FAS mutation) (Bhandoola et al., 1994, Int. Rev. of Immunol. 11: 231). Multiple sclerosis can be mimicked by mouse models of experimental allergic encephalomyelitis (Karrussis et al., 2001, J. Neuroimmunol. 120 (1-2): 1-9. Other animal models are known in the art and are encompassed within the scope of the invention.

In one embodiment, the efficacy of a particular dose or type of compound is evaluated by monitoring cytokine production in an animal model of inflammatory disease (e.g., as described above). Splenocytes, lymph nodes and/or intestinal inflammatory cells obtained from treated animals and control animals (e.g., animals receiving carrier but no fluorine-substituted alkyl phenol) can be contacted with antibodies specific for one or more cytokines and reactivity of these cells with inflammatory cytokines can be used to monitor reduction in inflammation. Cells can be analyzed by flow cytometry, by ELISAs, by ELISPOT assays, or by other methods routine in the art. Standard curves can be generated using purified cytokines. Data can be analyzed by routine statistical methods, e.g., such as the one sample t-test, to determine whether mean values significantly differ from zero. Paired t-tests can be used to analyze differences between group means while analysis of variance and/or a Dunnett's t-test can used to analyze multiple comparison data.

Preferably, various clinical parameters of disease are also monitored. For example, in mice, clinical evidence of disease includes weight loss, diarrhea, rectal prolapse and histological evidence of intestinal inflammation. Thus, improvement in these parameters would signify amelioration of disease. To grade intestinal inflammation in animal models, tissue is removed, sectioned and examined histologically, for example, after staining with hematoxylin and eosin. The degree of colonic inflammation can be graded semiquantitatively from 0 to 4 in a blinded fashion by a single pathologist using our usual standardized technique: 0=no inflammation; 1=low level inflammation; 2=intermediate level inflammation; 3=high level inflammation with wall thickening; and 4=transmural infiltration, and loss of goblet cells with wall thickening. Mast cells also can be scanned and counted. Preferably, samples are evaluated blindly.

For mice with collagen-induced arthritis, mice treated with various doses/types of compounds and control mice are examined every other day and their paws scored as follows: 0, normal; 1, Erythema and mild swelling confined to the ankle joint or toes; 2, Erythema and mild swelling extending from the ankle to the midfoot; 3, Erythema and severe swelling extending from the ankle to the metatarsal joints; and 4, Ankylosing deformation with joint swelling. These parameters can be correlated with the histological changes in the arthritic joints. Treatment success results in a decrease in the arthritis score with improvement in the histology. For pristane-induced arthritis, joints may be measured with a micrometer to detect swelling.

Experimental autoimmune encephalomyelitis can be induced in susceptible mice by repeated injection of appropriate sensitizing myelin antigens. In one aspect, mice treated with varying doses of compounds according to the invention and control mice are assessed clinically according to the following criteria: absence of disease; tail atony; hind-limb weakness; hind-limb paralysis; hind-limb paralysis and fore-limb paralysis or weakness; and morbidity. For histological analysis, the spinal cords and brains can be removed and examined histologically (e.g., by fixing the tissues formalin, staining paraffin-embedded sections and examining these using a light microscope. Dispersed splenocytes and cells from other regions can be studied in-vitro as discussed above.

Optimal dosage and modes of administration to subjects in need of treatment can readily be determined by conventional protocols, identifying therapeutic endpoints and identifying minimal doses and routes of administration which achieve these endpoints with minimal adverse effects. For, example in the case of arthritis, therapeutic endpoints may include increased mobility, decrease joint swelling, decreased pain, a reduction in inflammatory cytokines, and the like. Additionally, synovial fluid may be analyzed for cytokine and inflammatory protein concentrations, and for leukocyte composition and function, according to methods known in the art. Synovial biopsies can be performed to provide tissue for histological analysis according to methods known in the art.

In the case of inflammatory bowel disease, such as Crohn's disease, a therapeutic endpoint may include a decrease in the number of exacerbations or an increase in the amount of time between exacerbations of the disease, or a decrease in diarrhea observed over the treatment period. One particularly useful index for the assessment of Crohn's disease is the Crohn's Disease Activity Index, or CDAI (Best et al., 1976, Gastroenterology 70: 439). The CDAI incorporates 8 variables related to the disease activity and has been used in most recent studies of therapeutic agents in Crohn's disease. It includes the number of liquid or very soft stools, the severity of abdominal pain or cramping, general well-being, the presence of extraintestinal manifestations of the disease, presence or absence of an abdominal mass, use of antidiarrheal drugs, hematocrit, and body weight. The composite score ranges from 0 to about 600. Scores below 150 indicate remission and scores above 450 indicate severe illness. A tested, accepted and disease specific quality of life questionnaire also may be administered prior to and after treatment to assess therapeutic progress.

The Irvine Inflammatory Bowel Disease Questionnaire is a 32-item questionnaire. It evaluates quality of life with respect to bowel function (e.g. loose stools and abdominal pain), systemic symptoms (fatigue and altered sleep pattern), social function (work attendance and the need to cancel social events) and emotional status (angry, depressed, or irritable). The score ranges from 32 to 224, with higher scores indicating a better quality of life. Patients in remission usually score between 170 and 190. Also, helpful are endoscopic, x-ray and histological assessment of intestinal disease activity. C-reactive protein levels and blood cell sedimentation rate may also be monitored as systemic indicators of inflammation.

In the case of endotoxemia, a decrease in TNF may be monitored, as well as the patient's clinical presentation (e.g., resolution of fever). In the case of asthma, FEV (forced expiratory volume) may be measured as well as signs and symptoms of exacerbation. In humans, MS disease activity is gauged by monitoring progression and remittence of neurological signs and symptoms. The most widely used outcomes measurement is called The Expanded Disability Status Scale. Cerebral spinal fluid protein composition and cell content analyzed according to methods known in the art also may be used to monitor disease activity. Moreover, serial MRI studies show new gadolinium-enhanced brain lesions.

In treatments of respiratory diseases, pulmonary function tests can be used to evaluate lung compliance and function. Inflammatory cells can be obtained from bronchiolar lavages and studied for composition and function. Periodic chest x-ray or CT scans also can help assess disease activity.

Where compounds are used prophylactically, the absence of the appearance of symptoms or a reduction in the severity of symptoms (either overt physical symptoms or measurable biochemical symptoms) may be monitored. It should be obvious to those of skill in the art that the type of therapeutic endpoint will vary with the inflammatory condition being treated and that such endpoints are routinely assayed by those of skill in the art (e.g., physicians and other healthcare workers).

In one embodiment, a therapeutically effective dose of a compound is provided which is a dose effective to reduce by at least about 15%, at least about 50%, or at least about 90% of the expression of a marker associated with disease (e.g., such as pain, lack of mobility, fever, the number of disease episodes, diarrhea, reduction of skin lesions, asthmatic exacerbations, inflammatory cytokines, such as TNF-alpha, TNF-beta, IL-1, IL-6, IL-8, IL-10, IL-13, INF-gamma, and the like).

In yet a further embodiment, the invention provides a method of treating headache. The method includes the step administering a therapeutically effective amount of a pharmaceutical composition of the invention to a patient. In one embodiment, the headache is a migraine. In another embodiment, the therapeutically effective amount is an amount effective to reduce one or more symptoms of: pain, visual disturbance, auditory disturbance, and nausea.

The term "effective amount" includes an amount effective, at dosages and for periods of time necessary, to achieve the desired result, e.g., sufficient to anesthetize the subject, to sedate the subject, or to prevent cellular damage from oxygen radicals. An effective amount of compound of the invention may vary according to factors such as the health, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the compound are outweighed by the therapeutically beneficial effects.

A therapeutically effective amount of a compound of the invention (i.e., an effective dosage) may range from about 0.1 to 100 mg/kg body weight, preferably about 0.5 to 50 mg/kg body weight, more preferably about 1.0 to about 20 mg/kg body weight, and even more preferably about 4 to 18 mg/kg, 6 to 16 mg/kg, 8 to 14 mg/kg, or 10 to 12 mg/kg body weight.

In additional aspects, the invention provides compounds for use as muscle relaxants, (e.g., for bronchodilation), antispasmotics, inhibitors of endocannabinoid catabolism, and anti-nauseants.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the invention can include a single treatment or, in certain embodiments, can include a series of treatments.

EXAMPLE 1

Methods

Anticonvulsant Screening

All compounds (FIG. 1) were screened in three whole mouse models: the maximal electroshock model (MES), the scMET test (pentylenetetrazole, Metrazol), and the 6 Hz psychomotor seizure model of partial epilepsy (32 mA). Adult male CF No 1 albino mice (26-30 g) were used for the 6 Hz test and 18-25 g mice were used in the MES and scMet tests. The animals are housed, fed, and handled in a manner consistent with the recommendations in the National Council Publication, "Guide for the Care and Use of Laboratory Animals". The animal studies were performed by the NINDS Anticonvulsant Screening Program under IACUC number 09-12014. All compounds were administered ip in polyethylene glycol, 30%.

The MES model, which generates generalized tonic-clonic seizures, involved pretreating mice with experimental compound, and administering 60 Hz of alternating current (50 mA) for 2 s via corneal electrodes. Prior to current administration, the animal's corneas were treated topically with 1% tetracaine. Animals are considered protected if the hindlimb tonic extensor component is absent. The scMET test was done by pretreating mice with experimental compound and administering 85 mg/kg Metrazol into the loose folds of the skin in the midline of the neck. Eighty-five mg/kg Metrazol is the dose that causes seizures in 97% (CD97) of control animals. The animals were observed for 30 min for progression or absence of seizure which consists of clonic spasms of 3-5 s of the forelimbs, hindlimbs, jaws or vibrasse.

The 6 Hz test (also known as the minimal clonic seizure, or psychomotor test) involved delivering a corneal stimulus of 32 mA for 3 s. This current elicits psychomotor seizures in 97% of untreated animals. Seizures consist of a minimal clonic phase followed by stereotyped automatistic behaviors. Animals not showing such behaviors were considered protected. Toxicity was determined by the rotorod test. For this test, the animal is placed on a rotorod at 6 rpm following dosing. The animal is considered toxic if it falls off the rotorod three times in a 1 min period. The ED50, TD50 and confidence intervals were determined by probit analysis.

Synthesis

The compounds (FIG. 1) were synthesized as described in Scheme 1.

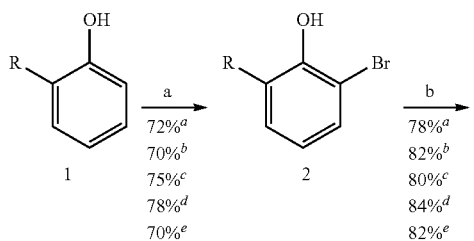

Scheme 1. Synthesis of 4-HTFE phenols.

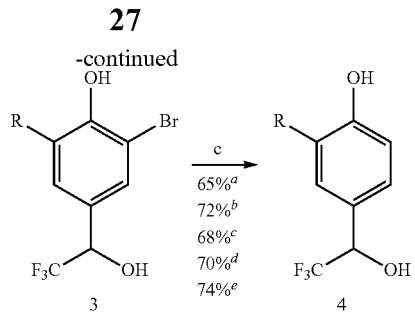

*a*: R = Me; *b*: R = Et; *c*: R = n-Pr; *d*: R = i-Pr; *e*: R = sec-Bu
a. NBS, CS$_2$, rt, 6 h; b. K$_2$CO$_3$, CF$_3$CH(OH)OEt, 60-70° C., 12 h; c. H$_2$, Pd/C, MeOH, rt, 12 h.

The 2-substituted alkyl phenols 1 were regiospecifically brominated at the 6-position using N-bromosuccinimide in carbon disulfide to get 2-alkyl-6-bromo phenols 2. The 2-alkyl-6-bromo phenols 2 were treated with trifluoroacetaldehyde ethyl hemiacetal and a catalytic amount of potassium carbonate at 60-70° to get 3, the 2-alkyl-6-bromo-4-HTFE substituted phenols. The bromine was removed by catalytic hydrogenation using Pd/C and a hydrogen balloon to get 4, the 2-alkyl-4-HTFE substituted phenols.

Results

All compounds were administered in a PEG solvent (30%) in order to allow the best comparison between molecules. The protective effects of each compound in the MES test are shown in Table 1.

TABLE 1

Substituted phenol effects in the maximal electroshock (MES) model*

| Compound | Dose, mg/kg, ip | 0.25 | 0.5 | 1 | 2 | 4 | 6 |
|---|---|---|---|---|---|---|---|
| RM170 | 30 | | 0/1 | | | | |
| | 100 | 0/3 | 0/3 | 0/3 | 0/3 | 0/3 | 0/3 |
| | 300 | | 1/1 | | | 1/1 | |
| RM166 | 30 | | 0/1 | | | 0/1 | |
| | 100 | | 0/3 | | | 0/3 | |
| | 300 | | 0/1 | | | 0/1 | |
| RM1208 | 30 | 0/2 | 0/1 | 0/3 | 0/3 | 0/1 | 0/3 |
| | 100 | | 0/3 | | | 0/3 | |
| | 300 | | 1/1 | | | 1/1 | |
| Rm125 | 30 | | 0/1 | | | 0/1 | |
| | 100 | 0/3 | 0/3 | 1/3 | 1/3 | 0/3 | 0/1 |
| | 300 | | 1/1 | | | 1/1 | |
| RM131 | 30 | | 0/1 | | | 0/1 | |
| | 100 | | 0/3 | | | 0/3 | |
| | 300 | | 1/1 | | | 0/1 | |
| RM122 | 30 | | 0/1 | | | 0/1 | |
| | 100 | | 0/3 | | | 0/3 | |
| | 300 | | 0/1 | | | 0/1 | |
| RM129 | 30 | | 0/1 | | | 0/1 | |
| | 100 | 0/3 | 0/3 | 0/3 | | 0/3 | |
| | 300 | | 1/1 | | | 0/1 | |
| R1204 | 30 | | 0/1 | | | 0/1 | |
| | 100 | | 0/3 | | | 0/3 | |
| | 300 | | 0/1 | | | 0/1 | |

*data represent number of animals protected/number of animals tested.

All compounds showed poor to no protective effects in this model. RM170, RM1208, RM125, RM131 and RM129 provided some protection, but only at the 300 mg/kg dose. RM170, RM1208, and RM125 exhibited protection at both 0.5 and 4 h, whereas RM131 and RM129 protected only at 0.5 h following this dosing. RM166, RM1204 and RM122 showed no MES protection at any dose.

The protective effects of each compound in the scMET test are shown in Table 2.

TABLE 2

Protective effects of substituted phenols in the scMET model*

| Compound | Dose, mg/kg, ip | Time (h) 0.5 | 4 |
|---|---|---|---|
| RM170 | 30 | 0/1 | 0/1 |
| | 100 | 0/1 | 0/1 |
| | 300 | 0/1 | 0/1 |
| RM166 | 30 | 0/1 | 0/1 |
| | 100 | 0/1 | 0/1 |
| | 300 | 0/1 | 0/1 |
| RM1208 | 30 | 0/1 | 0/1 |
| | 100 | 0/1 | 0/1 |
| | 300 | 1/1 | 0/1 |
| RM125 | 30 | 0/1 | 0/1 |
| | 100 | 0/1 | 0/1 |
| | 300 | 1/1 | 1/1 |
| RM131 | 30 | 0/1 | 0/1 |
| | 100 | 0/1 | 0/1 |
| | 300 | 1/1 | 0/1 |
| RM122 | 30 | 0/1 | 0/1 |
| | 100 | 0/1 | 0/1 |
| | 300 | 0/1 | 0/1 |
| RM129 | 30 | 0/1 | 0/1 |
| | 100 | 0/1 | 0/1 |
| | 300 | 0/1 | 0/1 |
| RM1204 | 30 | 0/1 | 0/1 |
| | 100 | 0/1 | 0/1 |
| | 300 | 0/1 | 0/1 |

*Data represent number of animals protected/number of animals tested.

No protective effects in the scMET model were seen with any compound except RM125 and RM1208. RM125 exhibited protection at the highest 300 mg/kg dose at 0.5 and 4 h following dosing, and RM1208 at 0.5 h only.

The protective effects of each compound in the 6 Hz test are shown in Tables 3 and 4.

TABLE 3

Toxicity and protective effects of RM170, RM166, RM1204 and RM1208 in the 6 Hz (32 mA) model*

| Compound | Dose, ip | Time (h) | | | | | |
|---|---|---|---|---|---|---|---|
| | | 0.25 | 0.5 | 1 | 2 | 4 | 6 |
| | | Toxicity | | | | | |
| RM170 | 30 | | 0/4 | | | 0/2 | |
| | 100 | 0/3 | 0/8 | 0/3 | 0/3 | 0/4 | 0/3 |
| | 300 | | 0/4 | | | 0/2 | |
| RM166 | 30 | | 0/4 | | | 0/2 | |
| | 100 | | 0/8 | | | 0/4 | |
| | 300 | | 0/4 | | | 0/2 | |
| RM1208 | 30 | | 0/4 | | | 0/2 | |
| | 100 | 0/2 | 0/8 | 0/3 | 0/3 | 0/4 | 0/3 |
| | 300 | | 3/4 | | | 0/2 | |
| RM1204 | 100 | 1/4 | 0/4 | 1/4 | 0/4 | 0/4 | |
| | | Protective effects | | | | | |
| RM170 | 100 | 0/4 | 0/4 | 2/4 | 1/4 | 1/4 | |
| RM166 | 100 | 0/4 | 0/4 | 0/4 | 0/4 | 1/4 | |
| RM1204 | 100 | 4/4 | 4/4 | 2/4 | 0/4 | 0/4 | |

*Data represent the number of animals protected/number of animals tested.

TABLE 4

Protective effects of substituted phenols in the 6 Hz (32 mA) model

| Compound | Time to peak effect (h) | $ED_{50}$, mg/kg (95% CI) | $TD_{50}$, mg/kg (95% CI) | PI |
|---|---|---|---|---|
| RM125 | 0.25 | 84.12 (52.93-147.82) | 161.12 (128.83-191.36) | 1.9 |
| RM131 | 0.5 | 53.85 (30.02-66.14) | 86.04 (72.37-97.2)* | 1.6 |
| RM122 | 0.5 | 112.45 (72.99-177.16) | 403.12 (286.08-531.42) | 3.6 |
| RM129 | 0.5 | 87.6 (50.35-166.64) | 144.4 (109.47-192.79) | 1.7 |

*Anesthesia occurred in 4 of 4 animals at 300 mg/kg dose.

RM166 showed no protective effects at 100 mg/kg at any time point from 0.25 to 4 h following dosing. RM170 inhibited seizures in no more than 2 of 4 animals at 100 mg/kg at any time point from 0.25 to 4 h. RM1204 showed complete protection (4/4) at 0.25 and 0.5 h and partial protection at 1 hour. Neither RM170 nor RM166 showed any evidence of toxicity at doses up to 300 mg/kg. RM1204 showed only low toxicity.

RM125, RM131, RM122 and RM129, provided complete protection (4 of 4 animals) at 100 mg/kg at one or more time points from 0.25 or 1 h. Because of their protective activities in the 6 Hz model, their toxic (TD50) as well as protective effects (ED50) were quantitated (Table 4). These compounds exhibited a time-to-peak effect of 0.5 h except for RM125 for which it was 0.25 h. Dose-response determinations showed that RM131 exhibited the greatest potency (ED50=53.8 mg/kg), whereas RM122 showed the weakest protection (ED50=112 mg/kg) of these compounds. RM131 was the most toxic, having a TD50 of 86 mg/kg, whereas RM122 was the least toxic with a TD50 of 403 mg/kg. The protective indices (TD50/ED50) ranged from a low of 1.6 for RM131 to a high of 3.6 for RM122. No deaths occurred following the administration of any of these compounds.

Discussion

This study demonstrates that a number of alkyl-substituted phenols can act as anticonvulsants in acute whole animal seizure models. Of the three initial screening models used by ASP, these small molecular weight phenols were predominately active against seizures in the 6 Hz model (a model of partial or psychomotor epilepsy), but not in the MES and scMET models. This profile suggests that such compounds may have novel mechanisms of action. In brief, compounds effective in the MES model, such as phenytoin, are thought to be sodium channel blockers and block seizure spread. Those effective in the scMET model are often GABAA agonists and are thought to raise seizure threshold. The 6 Hz model is an animal model of therapy-resistant epilepsy. To date, compound effectiveness in this model is not reflective of any specific anticonvulsant mechanism of action. For example, one compound protective in the 6 Hz model is levetiracetam. This compound is believed to act by stabilizing SV2A vesicles. Another 6 Hz active compound is ganaxolone. It is thought to act as an allosteric GABAA agonist. It is recognized, however, that most anticonvulsant act by multiple mechanisms.

It has previously been shown that 4-HTFE phenols having 2,6-di-isopropyl or sec-butyl groups (MB003, MB050) possess good anticonvulsant activity in the 6 Hz model. This investigation of 4-HTFE phenols that are further modified about the ortho positions reveals some of the molecular features that are important to antiseizure activity. Firstly, replacement of an alkyl group (6-position) of MB003 and MB050 with bromine (RM122 and RM129, respectively), creates compounds that also have antiseizure activity. The comparative effect of bromine is to cause a moderate lessening of seizure protection (84.12 [mg/kg] vs 112.45; 53.85 vs 87.6), but not elimination of seizure protection. Taken alone it could be reasoned that this halogen is serving in part as an isostere of the isopropyl group where it maintains important molecular target interactions. However, the relatively good antiseizure activity of the analogous compounds having no 6-substituent (RM125 and RM131) indicates that bromine is not serving a vital function in these compounds. Indeed the data indicate that a second ortho substituent is not required for anticonvulsant activity in the 2-isopropyl and 2-sec-butyl compounds.

The effect of varying the single ortho alkyl group on 4-HTFE phenols having no 6-substituent shows that the nature of the alkyl group is important to activity. Compounds having the 2-methyl, 2-ethyl or 2-n-propyl group were poorly protective in contrast to those possessing isopropyl and sec-butyl groups. The inactivity of the 2-methyl compound is similar to the lack of activity of DMPF, the 2,6-dimethyl analog. It is noteworthy that the apparent requirement for isopropyl and sec-butyl groups for optimal activity in these compounds is similar to the groups needed for good anesthetic activity among the alkyl phenols. A difference is that potent anesthetics require placement of the isopropyl or sec-butyl groups in both the 2- and 6-positions with the 4-position being free, whereas in the anticonvulsant 4-HTFE phenols, only a single ortho substituent is required. It appears that alkyl groups having increased spatial properties via branching, provide both optimal anesthetic (2,6-dialkyl phenols) and antiseizure (2-alkyl-4-HTFE phenols) activity. The anticonvulsant effects of compounds having branched or linear groups greater than 4 carbons have not been determined.

An exception to the need for a branched alkyl group is RM1204. RM1204 contains the 2-n-propyl group which as the lone ortho substituent (RM1208) was not an active compound. However, the addition of bromine as the second ortho substituent (RM1204) created a compound exerting complete protection at two time periods after dosing of 100 mg/kg, 0.25 and 0.5 h. The ED50 of this compound was not determined. The reason for this improved activity is not known. This bromine being in an equivalent ortho position to the n-propyl, may act in this molecule as an isostere of isopropyl by providing important target interactions not provided by n-propyl. As a whole, the data suggest that the 6-substitution may be viewed not as redundant, but as modulatory. This is reflected by the differing effects of alkyl group removal. MB003 has an ED50 of 38.6 mg/kg, whereas RM125 (removal of an isopropyl) is less effective with an ED50 of 84. MB050 has an ED50 of 73 mg/kg, but RM131 (removal of a sec-butyl group) is more effective with an ED50 of 53.85.

Compound effectiveness determined by the ED50s in this study should be interpreted with some caution. Compounds were administered i.p. Although all were given in 30% polyethylene glycol, there could be differences in absorption into the systemic circulation. Plasma or CNS levels of compound causing anticonvulsant activity were not determined. It is not likely that the alterations of the alkyl groups alone, e.g. isopropyl vs n-propyl, had major effects on plasma or CNS concentrations of these compounds.

The protective indices of the present compounds ranged from 1.6 to 3.6. Prior studies of propofol and 2,6-di-sec-butylphenol showed that these two compounds had protective indices of only 1.1 and 1.3, respectively. Therefore, similar to the effect of 4-HTFE substitution on 2,6-dialkyphenols, protective indices were also broad with the 4-HTFE phenols reported here. It is not apparent why 6-bromination of 2-isopropy-4-HTFE phenol (RM125) but not 2-sec-butyl-4-HTFE phenol (RM131) caused a multi-fold widening of the PI.

The specific role of 4-HTFE in anticonvulsant activity remains to be determined. It is hypothesized that 4-HTFE substitution diminishes the binding of alkyl phenols to sites that cause anesthesia and sedation while not substantially disrupting binding to targets that prevent seizures in the 6 Hz mouse model. Ample evidence indicates that the anesthetic/sedative effects of 2,6-dialkyphenols result from stimulation of the inhibitory GABAA receptors. Consequently, the anticonvulsant effects of 4-HTFE phenols may not be primarily mediated by GABAA receptors.

Compound 20 (2-isopropyl-6-(2,2,2-trifluoro-1-hydroxy-ethyl)pyridin-3-ol), a pyridine derivative, was also found to have anticonvulsant properties:

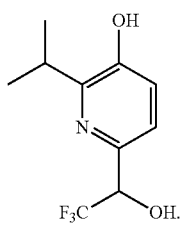

20

In summary, 4-HTFE phenols (and hydroxypyridines) having isopropyl or sec-butyl ortho groups produce good antiseizure protection in the 6 Hz therapy-resistant mouse model. Such compounds may be useful for the treatment of seizures.

Spectral data for selected compounds: 2-Bromo-6-isopropyl-4-(2,2,2-trifluoro-1-hydroxy-ethyl)-phenol (RM-122): $^1$H NMR (CDCl$_3$, 400 MHz): δ 7.47 (d, J=2 Hz, 1H), 7.24 (d, J=2 Hz, 1H), 5.73 (s, 1H), 4.98-4.92 (m, 1H), 3.33 (sep, J=7.2 Hz, 1H), 2.6 (d, J=4.4 Hz, 1H), and 1.26 (dd, J=7.2 Hz, 0.8 Hz, 6H); 2-Bromo-6-sec-Butyl-4-(2,2,2-trifluoro-1-hydroxy-ethyl)-phenol (RM-129): $^1$HNMR (CDCl$_3$, 400 MHz): $^1$H NMR (400 MHz) δ 7.45 (t, J=2.4 Hz, 1H), 7.17 (t, J=2.4 Hz, 1H), 5.67 (s, 1H), 4.96-4.90 (m, 1H), 3.14-3.05 (m, 1H), 2.56 (d, J=4.4 Hz, 1H) 1.71-1.54 (m, 1H), 1.21 (dd, J=7.2 Hz, 1.2 Hz, 3H), and 0.85 (td, J=7.6 Hz, 1.2 Hz, 3H); 2-Bromo-6-n-propyl-4-(2,2,2-trifluoro-1-hydroxy-ethyl)-phenol (RM-1204): $^1$HNMR (CDCl$_3$, 400 MHz): $^1$H NMR (400 MHz) δ 7.46 (s, 1H), 7.17 (s, 1H), 5.67 (s, 1H), 4.96-4.90 (m, 1H), 2.66 (t, J=7.2 Hz, 2H), 2.55 (d, J=4.0 Hz, 1H), 1.7-1.61 (m, 2H), and 0.97 (t, J=7.2 Hz, 3H); 2-Methyl-4-(2,2,2-trifluoro-1-hydroxy-ethyl)-phenol (RM-170): $^1$H NMR (CDCl$_3$, 400 MHz): δ 7.25 (s, 1H), 7.20 (d, J=8.0 Hz, 1H), 6.80 (d, J=8.0 Hz, 1H), 4.97-4.91 (m, 1H), 4.95 (s, 1H), 2.54 (d, J=4.4 Hz, 1H), and (s, 3H); 2-Ethyl-4-(2,2,2-trifluoro-1-hydroxy-ethyl)-phenol (RM-166): $^1$H NMR (CDCl$_3$, 400 MHz): δ 7.24 (d, J=2.0 Hz, 1H), 7.18 (dd, J=6.4 Hz, 2.0 Hz, 1H), 6.78 (d, J=7.2 Hz, 1H), 4.96-4.91 (m, 1H), 4.92 (s, 1H), 2.65 (q, J=7.2 Hz, 2H), 2.52 (d, J=4.4 Hz, 1H), and 1.24 (t, J=7.6 Hz, 3H); 2-n-Propyl-4-(2,2,2-trifluoro-1-hydroxy-ethyl)-phenol (RM-1208): $^1$H NMR (CDCl$_3$, 300 MHz): δ 7.21 (d, J=3.0 Hz, 1H), 7.17 (dd, J=6.4 Hz, 3.0 Hz, 1H), 6.77 (d, J=9 Hz), 4.96-4.87 (m, 1H), 4.80 (s, 1H), 2.57 (t, J=9 Hz, 2H), 2.42 (d, J=6.0 Hz, 1H), 1.69-1.57 (m, 1H), and 0.95 (t, J=9.0 Hz, 3H); 2-sec-Butyl-4-(2,2,2-trifluoro-1-hydroxy-ethyl)-phenol (RM-131): $^1$H NMR (CDCl$_3$, 400 MHz): δ 7.25 (t, J=2.8 Hz, 1H), 7.19 (td, J=6.4 Hz, 2.8 Hz, 1H), 6.79 (d, J=8.4 Hz, 1H), 4.99-4.92 (m, 1H), 4.90 (s, 1H), 3.02-2.94 (m, 1H), 2.50 (d, J=4.4 Hz, 1H), 1.72-1.24 (m, 1H), 1.25 (dd, J=6.8 Hz, 2.0 Hz, 3H), and 0.88 (dt, J=7.2 Hz, 1.2 Hz, 3H); 2-iso-Propyl-4-(2,2,2-trifluoro-1-hydroxy-ethyl)-phenol (RM-125): $^1$H NMR (CDCl$_3$, 400 MHz): δ 7.28 (s, 1H), 7.18 (d, J=8.0 Hz, 1H), 6.77 (d, J=8.0 Hz, 1H), 4.97-4.92 (m, 1H), 3.26-3.15 (m, 1H), and 1.26 (dd, J=7.2 Hz, 0.8 Hz, 3H).

EXAMPLE 2

Certain compounds of the invention are prepared as described below.

As shown in Scheme 2, an alkyl phenol 5 (in which R$_1$ and R$_2$ are as defined for a compound of Formula I) can be selectively formylated at the 4-position by treating 5 with dichloromethyl methyl ether and titanium tetrachloride in CH$_2$Cl$_2$ to give the 4-hydroxy benzaldehyde 6 (see, e.g., Monatshefte fuer Chemie, 1990, vol. 121, p. 227-236).

The phenolic hydroxyl group of compound 6 can be protected by different methods to get the ether 7. An alkyl ether of 6 can be obtained treating phenol 6 with an alkyl halide and potassium carbonate in acetonitrile. The aryl ethers can be obtained by copper-catalyzed coupling of aryl boronic acids and phenol 6 (see, e.g., Tetrahedron Letters, 1998, 39, 2937-2940). Alkylaryl ethers of 2 can be synthesized by Mitsunobu coupling of arylalkanols with phenol 6.

The 4-HTFE [4-(1-hydroxy-2,2,2-trifluoroethyl)] group can be introduced on benzaldehyde 7 by treating it with trifluorotrimethyl silane in presence of TBAF to yield the desired compound 8 (see, e.g., Journal of Agricultural and Food Chemistry, 1999, 47, 190-201).

Scheme 2:

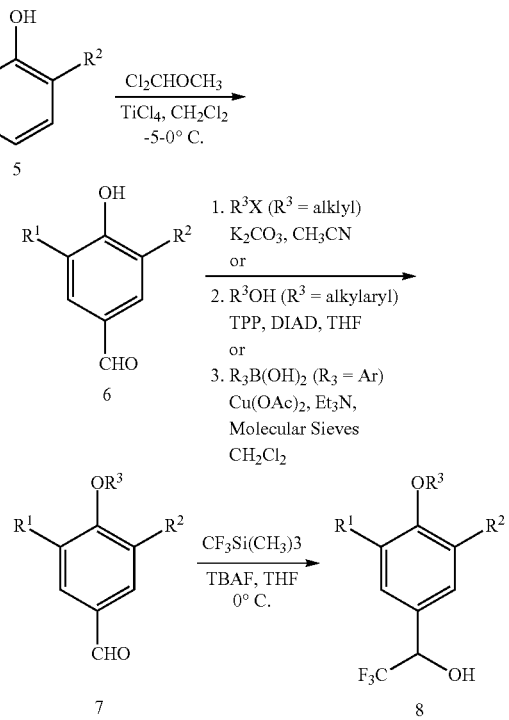

R$^1$ = alkyl group
R$^2$ = H, Halogen, or alkyl group
R$^3$ = Alkyl, Aryl, or alkylaryl All patents, patent applications, and published references cited herein are hereby incorporated by reference in their entirety.

While this invention has been particularly illustrated and described with reference to particular examples, it will be understood by those skilled in the art that various changes in form and details may be made therein without departing from the scope and spirit of the invention encompassed by the appended claims.

REFERENCES AND NOTES

1. James, R. and J. B. Glen, *Synthesis, Biological Evaluation, and Preliminary Structure—Activity Considerations of a Series of Alkylphenols as Intravenous Anesthetic Agents.* Journal of Medicinal Chemistry, 1980. 23(12): p. 1350-1357.
2. Krasowski, M. D., et al., *General anesthetic potencies of a series of propofol analogs correlate with potency for potentiation of gamma-aminobutyric acid (GABA) current at the GABA(A) receptor but not with lipid solubility.* Journal of Pharmacology and Experimental Therapeutics, 2001. 297(1): p. 338-351.
3. Prasad, A., et al., *Propofol and midazolam in the treatment of refractory status epilepticus.* Epilepsia, 2001. 42(3): p. 380-386.
4. Marik, P. E. and J. Varon, *The management of status epilepticus.* Chest, 2004. 126(2): p. 582-591.
5. Deriu, P. L., et al., *Propofol Anticonvulsant Activity in Experimental Epileptic Status.* British Journal of Anaesthesia, 1992. 69(2): p. 177-181.
6. Holtkamp, M., X. Tong, and M. C. Walker, *Propofol in subanesthetic doses terminates status epilepticus in a rodent model.* Annals of Neurology, 2001. 49(2): p. 260-263.
7. Baker, M. T., *The anticonvulsant effects of propofol and a propofol analog, 2,6-diisopropyl-4-(1-hydroxy-2,2,2-trifluoroethyl)phenol, in a 6 Hz partial seizure model.* Anesth Analg, 2011. 112(2): p. 340-344.
8. Rigby-Jones, A. E. and J. R. Sneyd, *New drugs and technologies,* intravenous anaesthesia is on the move (again). Brit J Anaesth, 2010. 105(3): p. 246-254.
9. Barton M E, K. B., Wolf H H, White H S, *Pharmacological characterization of a 6 HZ psychomotor seizure model of partial epilepsy.* Epilepsy Res, 2001. 47: p. 217-227.
10. Loscher, W., *Critical review of current animal models of seizures and epilepsy used in the discovery and development of new antiepileptic drugs.* Eur J Epilepsy, 2011. 20(5): p. 359-368.
11. Wuttke, T. V. and H. Lerche, *Novel anticonvulsant drugs targeting voltage-dependent ion channels.* Expert Opinion on Investigational Drugs, 2006. 15(10): p. 1167-1177.
12. Stables J P, K. H., ed. *The NIH anticonvulsant drug development (ADD) program: preclinical anticonvulsant secreening project.* Chapter 16. Molecular and cellular targets for anti-epileptic drugs, ed. R. G. Avanzini G, Tanganelli P, Avoli M. 1997, John Libbey & Company, Ltd. 191-198.
13. Gareth, T., *Medicinal Chemistry: An Introduction.* 2nd ed 2007: John Wiley & Sons, Ltd, West Sussex, England.
14. White, H. S., et al., *The early identification of anticonvulsant activity—role of the maximal electroshock and subcutaneous pentylenetetrazol seizure models.* Italian Journal of Neurological Sciences, 1995. 16(1-2): p. 73-77.
15. Swinyard E A, W. J., White H S, Franklin M R, *General principles: experimental selection, quantification, and evaluation of anticonvulsants.* Antiepileptic drugs, ed. M. B. Levy R H, J K Penry, Dreifuss FE1989, New York: Raven Press.
16. Swinyard, E. A., et al., *Studies on Mechanism of Amphetamine Toxicity in Aggregated Mice.* Journal of Pharmacology and Experimental Therapeutics, 1961. 132(1): p. 97-&.
17. Rogawski, M. A., *Diverse mechanisms of antiepileptic drugs in the development pipeline.* Epilepsy Res, 2006. 69(3): p. 273-294.
18. Mares, P. and M. Stehlikova, *Anticonvulsant doses of ganaxolone do not compromise motor performance in immature rats.* Neuroscience Letters, 2010. 469(3): p. 396-399.
19. Malawska, B., *New anticonvulsant agents.* Current Topics in Medicinal Chemistry, 2005. 5(1): p. 69-85.
20. Krasowski, M. D. and A. J. Hopfinger, *The discovery of new anesthetics by targeting GABA(A) receptors.* Expert Opinion on Drug Discovery, 2011. 6(11): p. 1187-1201.

What is claimed is:

1. A compound represented by Formula I:

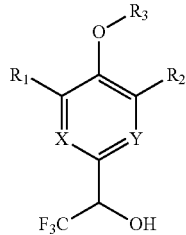

Formula I in which
    at least one of X and Y is CH, and the other of X and Y is N or CH;
    $R_1$ is $C_1$-$C_4$ alkyl or $C_1$-$C_4$ haloalkyl;
    $R_2$ is a halogen; and
    $R_3$ is H, $C_1$-$C_4$ alkyl, aryl, or —$(CH_2)_n$-aryl, in which n is 1, 2, or 3;
or a pharmaceutically acceptable salt or prodrug thereof.

2. The compound of claim 1, wherein the compound is represented by Formula Ia:

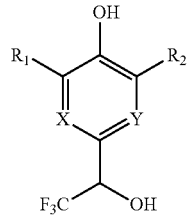

Formula Ia or a pharmaceutically acceptable salt or prodrug thereof.

3. The compound of claim 1, wherein the compound is represented by Formula II:

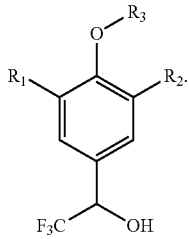

Formula II

4. The compound of claim 1, wherein the compound is represented by Formula IIa:

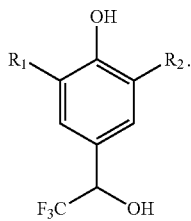

Formula IIa

5. The compound of claim 1, wherein the compound is represented by Formula III:

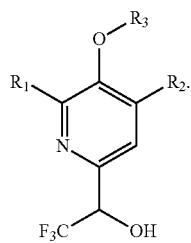

Formula III

6. The compound of claim 1, wherein the compound is represented by Formula IIIa:

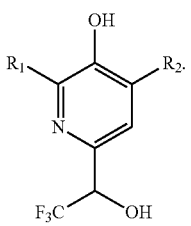

Formula IIIa

7. The compound of claim 1, wherein $R_1$ is $C_1$-$C_4$ alkyl.
8. The compound of claim 1, wherein $R_2$ is Br.
9. The compound of claim 1, wherein the compound is selected from the group consisting of:
   2-Bromo-6-isopropyl-4-(2,2,2-trifluoro-1-hydroxy-ethyl)-phenol,
   2-Bromo-6-sec-Butyl-4-(2,2,2-trifluoro-1-hydroxy-ethyl)-phenol, and
   2-Bromo-6-n-propyl-4-(2,2,2-trifluoro-1-hydroxy-ethyl)-phenol.
10. The compound of claim 1, wherein the compound is selected from the group consisting of:
    1-(3-bromo-5-isopropyl-4-methoxyphenyl)-2,2,2-trifluoroethanol,
    and
    1-(4-(benzyloxy)-3-bromo-5-isopropylphenyl)-2,2,2-trifluoroethanol.
11. A method of treating or preventing convulsions in a subject in need thereof comprising administering to said subject a therapeutically effective amount of a compound of claim 1.

12. A method of treating or preventing seizures in a subject in need thereof, the method comprising administering to said subject a therapeutically effective amount of a compound of claim 1.
13. A method of treating or preventing epileptic seizures in a subject in need thereof, the method comprising administering to said subject a therapeutically effective amount of a compound of claim 1.
14. A method for anesthetizing a subject, the method comprising administering to said subject a therapeutically effective amount of a compound of claim 1.
15. A method for sedating a subject, the method comprising administering to said subject a therapeutically effective amount of a compound of claim 1.
16. A method for preventing cellular damage from oxygen radicals, the method comprising contacting a cell in need of such prevention with an effective amount of a compound of claim 1.
17. A method of treating a respiratory disorder in a subject in need thereof, the method comprising administering to said subject a therapeutically effective amount of a compound of claim 1.
18. A compound represented by Formula I:

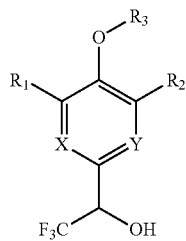

Formula I in which
  at least one of X and Y is CH, and the other one of X and Y is N;
  $R_1$ is $C_1$-$C_4$ alkyl or $C_1$-$C_4$ haloalkyl;
  $R_2$ is H, $C_1$-$C_4$ alkyl, or halogen; and
  $R_3$ is H, $C_1$-$C_4$ alkyl, aryl, or —$(CH_2)_n$-aryl, in which n is 1, 2, or 3;
or a pharmaceutically acceptable salt or prodrug thereof.

19. A compound represented by Formula V:

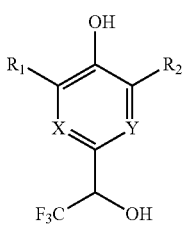

Formula V in which
  at least one of X and Y is CH, and the other of X and Y is N or CH;
  $R_1$ is $C_1$-$C_4$ alkyl or $C_1$-$C_4$ haloalkyl;
  $R_2$ is H or halogen;
or a pharmaceutically acceptable salt or prodrug thereof.

20. The compound of claim 19, wherein X and Y are each CH.
21. The compound of claim 20, wherein $R_1$ is $C_1$-$C_4$ alkyl.

22. The compound of claim 21, wherein $R_1$ is $C_3$-$C_4$ alkyl.
23. The compound of claim 19, wherein X is N and Y is CH.
24. The compound of claim 19, wherein $R_2$ is Br.
25. The compound of claim 19, wherein the compound is selected from the group consisting of:
   2-Bromo-6-isopropyl-4-(2,2,2-trifluoro-1-hydroxy-ethyl)-phenol,
   2-Bromo-6-sec-Butyl-4-(2,2,2-trifluoro-1-hydroxy-ethyl)-phenol,
   2-Bromo-6-n-propyl-4-(2,2,2-trifluoro-1-hydroxy-ethyl)-phenol,
   2-iso-Propyl-4-(2,2,2-trifluoro-1-hydroxy-ethyl)-phenol,
   2-sec-Butyl-4-(2,2,2-trifluoro-1-hydroxy-ethyl)-phenol,
   2-Methyl-4-(2,2,2-trifluoro-1-hydroxy-ethyl)-phenol,
   2-Ethyl-4-(2,2,2-trifluoro-1-hydroxy-ethyl)-phenol, and
   2-n-Propyl-4-(2,2,2-trifluoro-1-hydroxy-ethyl)-phenol.
26. A pharmaceutical composition comprising a compound of any one of claims 1-6, 7, 8-23 and 18 and a pharmaceutically acceptable salt thereof.
27. A compound selected from the group consisting of:
   2-bromo-6-isopropyl-4-(2,2,2-trifluoro-1-hydroxyethyl)phenol,
   2-bromo-6-sec-butyl-4-(2,2,2-trifluoro-1-hydroxyethyl)phenol,
   2-bromo-6-n-propyl-4-(2,2,2-trifluoro-1-hydroxyethyl)phenol,
   2-isopropyl-4-(2,2,2-trifluoro-1-hydroxyethyl)phenol,
   2-sec-butyl-4-(2,2,2-trifluoro-1-hydroxyethyl)phenol,
   2-methyl-4-(2,2,2-trifluoro-1-hydroxyethyl)phenol,
   2-ethyl-4-(2,2,2-trifluoro-1-hydroxyethyl)phenol,
   2-n-propyl-4-(2,2,2-trifluoro-1-hydroxyethyl)phenol,
   1-(3,5-diisopropyl-4-methoxyphenyl)-2,2,2-trifluoroethanol,
   1-(4-(benzyloxy)-3,5-diisopropylphenyl)-2,2,2-trifluoroethanol,
   2,2,2-trifluoro-1-(3-isopropyl-4-methoxyphenyl)ethanol,
   1-(4-(benzyloxy)-3-isopropylphenyl)-2,2,2-trifluoroethanol,
   1-(3-bromo-5-isopropyl-4-methoxyphenyl)-2,2,2-trifluoroethanol,
   2,2,2-trifluoro-1-(3-isopropyl-4-phenoxyphenyl)ethanol, and
   1-(4-(benzyloxy)-3-bromo-5-isopropylphenyl)-2,2,2-trifluoroethanol.

* * * * *